US00PP30707P3

(12) United States Plant Patent
Wood

(10) Patent No.: US PP30,707 P3
(45) Date of Patent: Jul. 16, 2019

(54) ***CHAMAECYPARIS* PLANT NAMED 'SMNCLBF'**

(50) Latin Name: *Chamaecyparis lawsoniana*
Varietal Denomination: SMNCLBF

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,455

(22) Filed: Nov. 14, 2017

(65) Prior Publication Data

US 2019/0150342 P1 May 16, 2019

(51) Int. Cl.
*A01H 7/00* (2006.01)

(52) U.S. Cl.
USPC ..... Plt./213

(58) Field of Classification Search
USPC ..... Plt./213
CPC ... A01H 7/00; A01H 5/00; A01H 5/02; A01H 5/04; A01H 6/00; A01H 5/025
See application file for complete search history.

(56) References Cited

PUBLICATIONS

Spring Meadow Nursery Flowering Shrubs Starter Plants Catalog and Shrub Reference 2017-2018, retrieved on Oct. 11, 2018, retrieved from the Internet at https://springmeadownursery.com/files/resource_files/2017-18_SMN_Catalog_1-50.pdf, pp. 1-9, 37. (Year: 2017).*

* cited by examiner

*Primary Examiner* — June Hwu
(74) *Attorney, Agent, or Firm* — Cassandra Bright

(57) ABSTRACT

A new and distinct *Chamaecyparis* cultivar named 'SMNCLBF' is disclosed, characterized by soft foliage with a blue tint. Plants have low maintenance requirements and are upright with branches occurring at strongly acute angles. The new cultivar is a *Chamaecyparis*, suitable for ornamental garden purposes.

3 Drawing Sheets

Latin name of the genus and species: *Chamaecyparis lawsoniana.*

Variety denomination: 'SMNCLBF'.

BACKGROUND OF THE INVENTION

The new cultivar is a product of chance discovery by the inventor, Timothy Wood. This new variety, hereinafter referred to as 'SMNCLBF', was selected as a naturally occurring branch mutation from an unnamed, unpatented *Chamaecyparis lawsoniana*. The novel variety was discovered in a poly-greenhouse in Grand Haven, Mich. during 2006.

After identifying the new variety as a potentially interesting selection, first propagation of 'SMNCLBF' occurred by softwood cuttings at a commercial nursery in Grand Haven, Mich. in 2010. The inventor continued controlled testing and propagation, assessing stability of the unique characteristics of this variety. Five generations have been reproduced and have shown that the unique features of this cultivar are stable and reproduced true to type.

SUMMARY OF THE INVENTION

The cultivar 'SMNCLBF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNCLBF' These characteristics in combination distinguish 'SMNCLBF' as a new and distinct *Chamaecyparis* cultivar:

1. Foliage with a blue tint.
2. Good container plant, having low maintenance requirements.
3. Soft texture.

PARENT COMPARISON

'SMNCLBF' is similar in most horticultural characteristics to the parent, however, plants of 'SMNCLBF' differ in the following:

1. New cultivar has a softer texture; parent foliage is more prickly.
2. The new cultivar has foliage with a blue tint not seen on the parent variety.

COMMERCIAL COMPARISON

'SMNCLBF' can be compared to the commercial variety *Chamaecyparis lawsoniana* 'Oregon Blue', unpatented. The varieties are similar in most horticultural characteristics, however, plants of 'SMNCLBF' differ in the following ways:

1. Plants of the new cultivar have more of an acute plant apex; comparator is more columnar.
2. New cultivar is more compact; comparator is taller.
3. New cultivar has branches angled upwards; comparator's branches are more outward and sweeping over.

BRIEF DESCRIPTION OF THE PHOTOGRAPHS

The accompanying photograph in FIG. 1 illustrates in full color a typical plant of 'SMNCLBF' in a 3 gallon container grown in Grand Haven, Mich. in a polyhouse.

Plants in FIG. 1 are approximately 2 years old.

Figure 1:
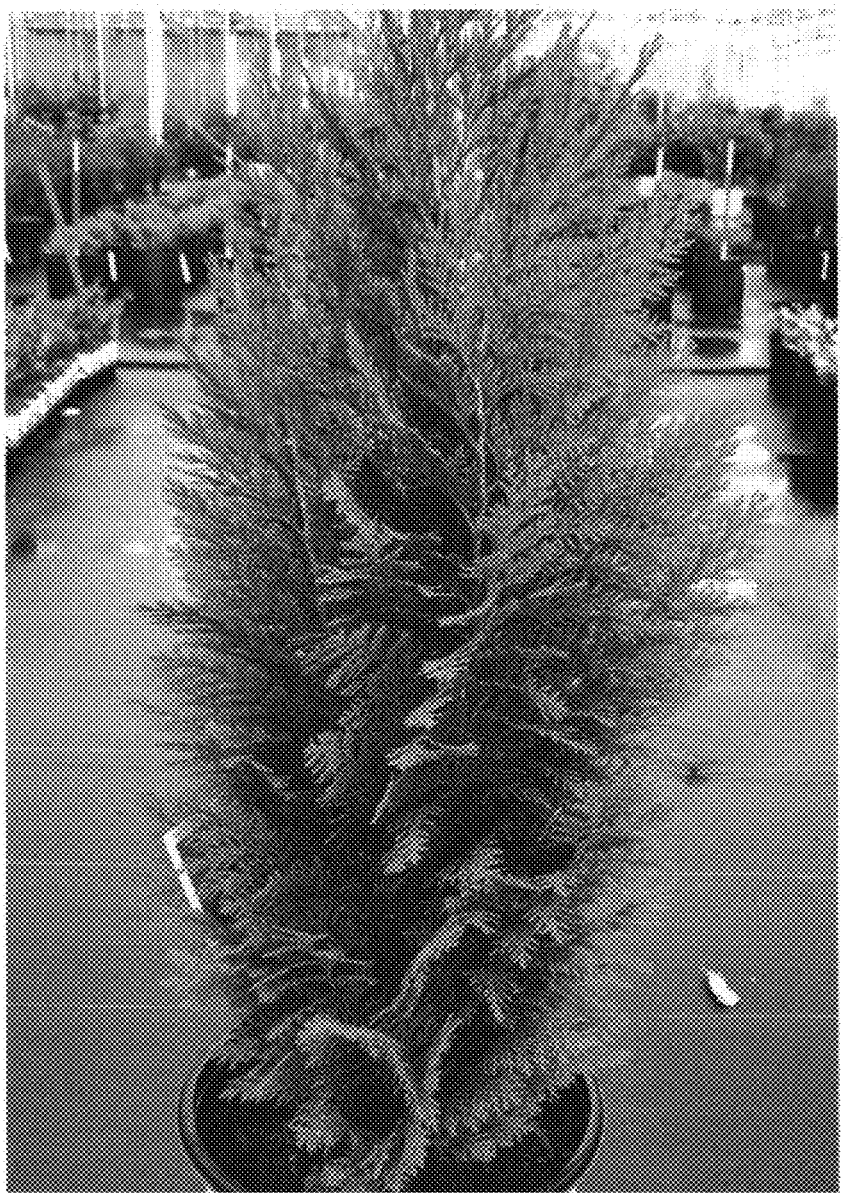
Figure 2:
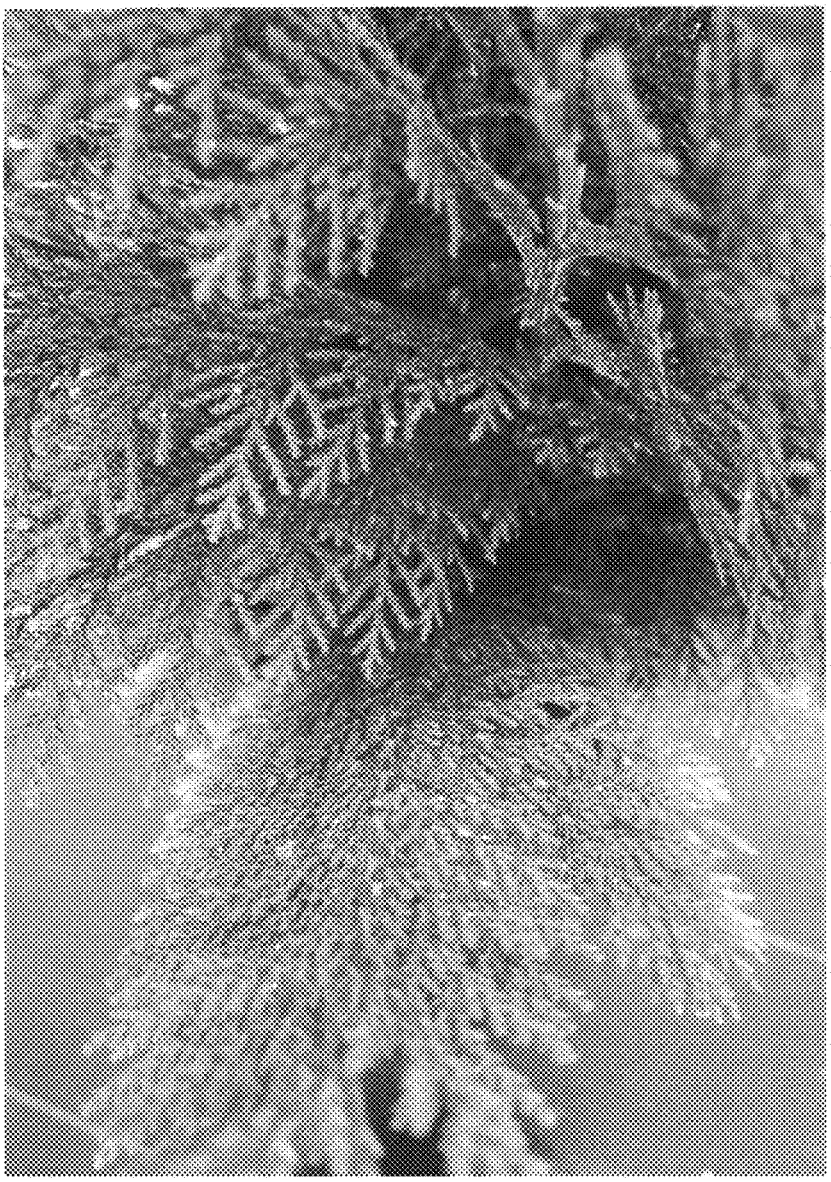
FIG. 2 illustrates a close up view of the foliage.
Figure 3:
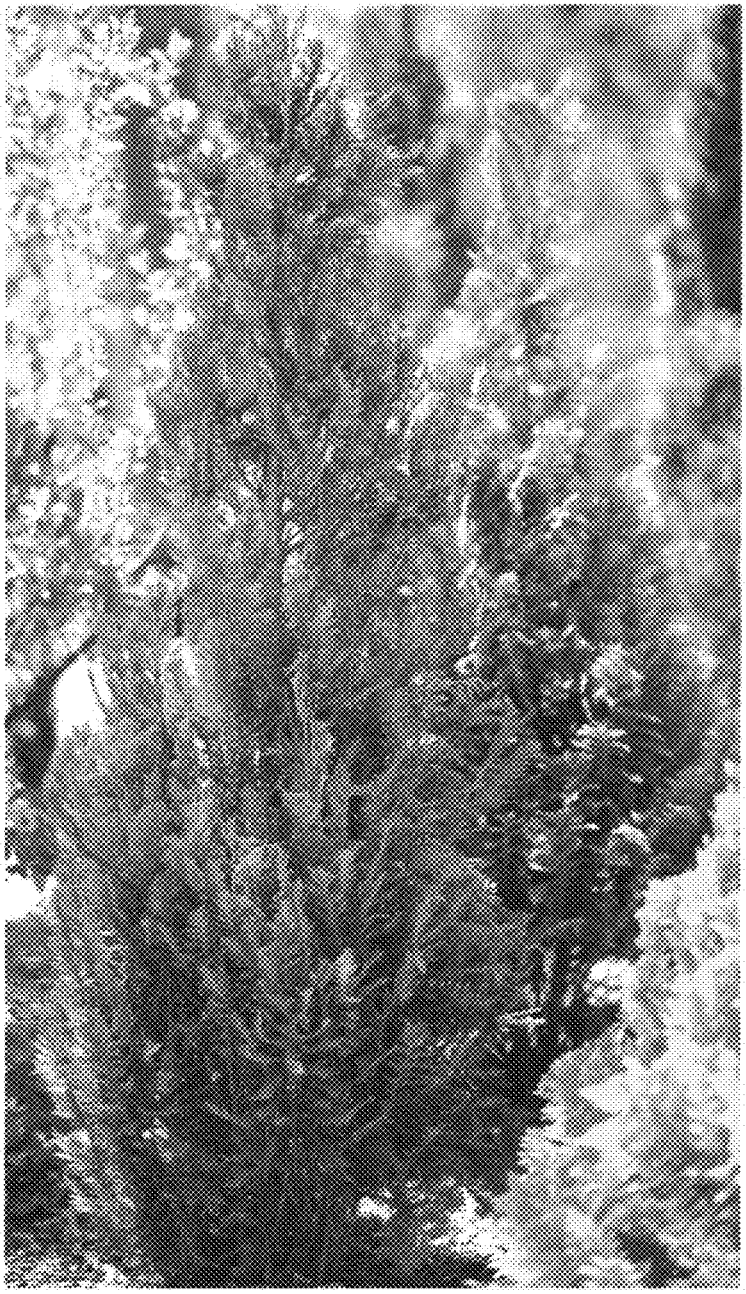
FIG. 3 illustrates a plant of the new variety at approximately 2 years old grown outdoors in Grand Haven, Mich. and exhibit the characteristic growth, having a more acute plant apex.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNCLBF' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

Botanical classification: *Chamaecyparis lawsoniana* 'SMNCLBF'.

PROPAGATION

Typical method: Softwood cuttings.
Time to initiate rooting: 120 days at approximately 10° C.
Time to produce a rooted young plant: 180 days at approximately 10° C. to 13° C.
Root description: Fibrous, both fine and fleshy roots present. Moderately well branched. Colored light brown, not accurately measured with an R.H.S. chart.

PLANT

Age of plant described: 2 years.
Container size of plant described: 3 gallon.
Growth habit: Upright evergreen tree. Slightly mounding in juvenility, upright with maturity.
Height: 81 cm in a 3 gallon pot.
Plant spread: 33 cm in a 3 gallon pot.
Typical growth rate: Moderate.
Pinching required: Encourages branching.
Branching characteristics:
Angle: 0 to 10°.
Quantity of lateral branches: About 20.
Length of lateral branches: 28 cm.
Diameter of lateral branches: 5 mm.
Lateral branch shape: Round with overlapping scales.
Branch orientation:
*Immature*.—Average range 15 to 25 degrees from center.
*Mature*.—Average range 15 to 35 degrees from center.
Stem strength: Strong, flexible.
Stem color: Partly Green 128C, and Grey Brown 199C.
Internode length: 1 cm.
Trunk bark:
*Color*.—Near RHS Brown N200B.
*Texture*.—Rough, sparsely scaly.

FOLIAGE

General description: Overlapping scales.
Leaf:
*Arrangement*.—Alternate.
*Shape of blade*.—Scale-like.
*Average length*.—2 mm.
*Average width*.—5 mm.
*Apex*.—Apiculate.
*Base*.—Cuneate.
*Margin*.—Entire.
*Texture of top surface*.—Smooth.
*Texture of bottom surface*.—Smooth.
*Foliage color*.—Young foliage upper side: Green N138C, tinged Green 133C. Young foliage under side: Green 139C. Mature foliage upper side: Green N138A, tinged Green 133B. Mature foliage under side: Green 139A.
*Venation*.—Not observable.
*Fragrance*.—Not observed.

FLOWER

Flowering not observed.

OTHER CHARACTERISTICS

Disease and pest resistance: Neither resistance nor susceptibility observed.
Drought tolerance: No tolerance for drought.
Temperature tolerance: −29 to 36 degree C.

What is claimed is:

1. A new and distinct cultivar of *Chamaecyparis* plant named 'SMNCLBF' as herein illustrated and described.

* * * * *